United States Patent
Wessel et al.

[19]

[11] Patent Number: 6,028,240
[45] Date of Patent: *Feb. 22, 2000

[54] DISPOSABLE DIAPER THAT STRETCHABLY CONFORMS TO A WEARER

[75] Inventors: Joyce Ann Wessel, Seminole, Fla.; Mark Daniel Strickland, Woodstock, Ga.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/971,487

[22] Filed: Nov. 17, 1997

Related U.S. Application Data

[63] Continuation of application No. 08/568,111, Dec. 6, 1995, abandoned, which is a continuation of application No. 07/810,603, Dec. 19, 1991, abandoned.

[51] Int. Cl.[7] ..................................................... A61F 13/15
[52] U.S. Cl. ..................... 604/358; 604/385.1; 604/373; 604/372; 604/370
[58] Field of Search ..................................... 604/358, 366, 604/367, 370, 372, 373, 385.2, 393, 400, 402

[56] References Cited

U.S. PATENT DOCUMENTS

| | | |
|---|---|---|
| 1,929,363 | 10/1933 | Long . |
| 2,205,745 | 6/1940 | Fridolph . |
| 3,431,562 | 3/1969 | Souders . |
| 3,520,303 | 7/1970 | Endres . |
| 3,570,012 | 3/1971 | Winters . |
| 3,720,957 | 3/1973 | Patience . |
| 3,949,128 | 4/1976 | Ostermeier . |
| 4,517,714 | 5/1985 | Sneed et al. . |
| 4,555,811 | 12/1985 | Shimalla . |
| 4,670,913 | 6/1987 | Morell et al. . |
| 4,701,171 | 10/1987 | Boland et al. . |
| 4,704,114 | 11/1987 | Wilson et al. . |
| 4,705,712 | 11/1987 | Cashaw et al. . |
| 4,720,415 | 1/1988 | Vander Wielen et al. . |
| 4,747,846 | 5/1988 | Boland et al. . |
| 4,748,065 | 5/1988 | Tanikella . |
| 4,756,709 | 7/1988 | Stevens . |
| 4,777,080 | 10/1988 | Harris, Jr. et al. . |
| 4,781,966 | 11/1988 | Taylor . |
| 4,791,685 | 12/1988 | Malibauer . |
| 4,965,122 | 10/1990 | Morman . |
| 4,981,747 | 1/1991 | Morman . |

FOREIGN PATENT DOCUMENTS

| | | |
|---|---|---|
| 526807 | 6/1956 | Canada . |
| 127483 | 12/1984 | European Pat. Off. . |

*Primary Examiner*—John G. Weiss
*Assistant Examiner*—Dennis Ruhl
*Attorney, Agent, or Firm*—Karl V. Sidor

[57] ABSTRACT

Disclosed is a disposable protective garment adapted to stretchably conform to the body of a wearer, the garment being composed of at least one piece of a reversibly-necked material which is adapted to have recoverable stretch in at least one direction. The reversibly-necked material is necked by drawing and treated to impart memory of its necked configuration so it has recoverable stretch while also being breathable, liquid resistant and conformable. The disposable protective garment may contain a body portion, sleeve portions and/or leg portions. The stretch direction of reversibly-necked material may be parallel to the direction of motion of the body portion, sleeve portions and/or leg portions.

26 Claims, 5 Drawing Sheets

DISPOSABLE DIAPER THAT STRETCHABLY CONFORMS TO A WEARER

This application is a continuation application of U.S. patent application Ser. No. 08/568,111 entitled filed in the U.S. Patent and Trademark Office on Dec. 6, 1995, now abandoned, which is a continuation application of U.S. patent application Ser. No. 07/810,603 filed in the U.S. Patent and Trademark Office on Dec. 19, 1991, now abandoned.

TECHNICAL FIELD

The present invention relates to protective garments. More particularly, the present invention relates to protective garments having improved comfort.

BACKGROUND

Nonwoven materials are known to be suitable for producing many types of limited use or disposable protective garments such as surgical gowns, industrial work wear, coveralls, as well as cover materials for disposable personal care products such as disposable diapers and incontinence garments. The usefulness of such garments is influenced by factors such as comfort and resistance to liquids.

Factors affecting the comfort of someone wearing such garments include the stretch properties, softness and breathability of the garment material. Materials that are soft, stretchable and breathable are typically more comfortable than materials that do not have those characteristics. Stretchable materials may be classified into two broad categories: materials having "recoverable stretch" and materials having "non-recoverable stretch." A material can be described as having recoverable stretch if it contracts upon termination of a biasing force following stretching of the material by application of the biasing force. Material having non-recoverable stretch does not contract in this manner. In most situations, material having recoverable stretch is more desirable for protective garments than material having non-recoverable stretch, especially in environments where baggy or loose fitting garments may snag and tear to reduce the protection of the wearer or become caught in machinery.

In the past, recoverable stretch properties have been incorporated into garments by use of elastomeric sections, pieces and/or strips such as, for example, elastomeric nonwoven webs formed from A-B-A' block copolymers, polyurethane elastomeric materials, polyamide elastomeric materials, polyester elastomeric materials, and elastic copolymers of ethylene and at least one vinyl monomer such as, for example, vinyl acetates, unsaturated aliphatic monocarboxylic acids, and esters of such monocarboxylic acids. Although such extrudable elastomeric materials provide highly desirable stretch, they are relatively expensive and, in some cases, may break down if exposed to certain liquids and/or gases that can be present in many industrial and medical environments. Furthermore, a process of manufacturing garments by joining several different fabrics together generally tends to be more complex and less efficient than a process of making garments from a single fabric. Complex and relatively inefficient manufacturing processes generally reduce the cost advantages provided by inexpensive materials.

A material that has recoverable stretch without using the elastomeric materials described above has been suggested in U.S. Pat. No. 4,965,122. According to that patent, a tensioning force is applied to a fabric to reduce its width. Such a tensioned or drawn material is referred to as a "necked" material. That material is heated and cooled while it is necked so that it retains a memory of its necked condition which causes it to recover to generally about its necked dimensions after non-destructive stretching. For example, U.S. Pat. No. 4,965,122 teaches that a reversibly necked material may be adapted to stretch at least about 75 percent and recover at least 50 percent when stretched 75 percent.

Protective garments should also be resistant to liquids. For example, surgical gowns, drapes, face masks, shoe covers and the like must be relatively resistant to liquids. For a variety of reasons, it is undesirable for liquids and/or pathogens which may be carried by liquids to pass through a surgical gown or patient drape to contact medical personnel or patients.

Similarly, it is often highly desirable to isolate persons from harmful substances which may be present in a work place or accident site. To reduce the chance of exposure, workers would benefit from wearing protective clothing that is relatively liquid resistant but which is still comfortable so it does not reduce their performance. In the case of personal care products, such as diapers and adult incontinence products, it is desirable to provide a garment which is comfortable and which resists leakage of liquids. In all such products, it is also highly desirable that the product be inexpensive so as to be disposable.

It is highly desirable to have a garment made of a material that allows air and water vapor to pass but which is still relatively resistant to the passage of liquids. A "breathable" material can increase the comfort of someone wearing a garment, especially if the garment must be worn under high heat index conditions, during vigorous physical activity, or for long periods. Ventilation holes, ports and/or panels may be relatively ineffective and may compromise the protection of the wearer. Furthermore, a process of manufacturing garments with ventilation holes, ports and/or panels generally tends to be more complex and less efficient than a process of making garments without such features. Complex and relatively inefficient manufacturing processes generally reduce the cost advantages provided by inexpensive materials.

Many attempts have been made to provide protective garments which are breathable, relatively liquid impervious, have recoverable stretch and are so inexpensive that they can be discarded after only a single use. One problem that has been encountered is that inexpensive materials which might be used for such garments generally have poor resistance to liquids, poor stretch recovery, and low levels of breathability.

Certain inexpensive, liquid resistant materials are known. An exemplary material is a calendered flash-spun polyethylene spunbond material known in the art as Tyvek®, available from E. I. DuPont De Nemours. Although Tyvek® is an inexpensive, strong, liquid resistant material it offers little breathability or stretch. Another exemplary material is generally known in the art as spunlace fabric. For example, spunlace fabric may be obtained from E. I. DuPont De Nemours under the trade designation Sontara®. Although spunlace fabric is inexpensive, breathable, stretchable, and liquid resistant, it generally exhibit non-recoverable stretch. Garments made of such inexpensive materials often require other materials, components, treatments, or the like to provide comfort features such as, for example, conformability, breathability or recoverable stretch that are lacking in a garment composed only of the inexpensive material.

Thus, a need exists for protective garments that requires little or no other materials, components, treatments, or the like to provide desirable comfort features such as, for example, conformability, breathability, liquid resistance, or recoverable stretch. For example, a need exists for protective garments that are composed substantially or entirely of an inexpensive material such that the garments are liquid resistant and so inexpensive as to be disposable while also being conformable, breathable, and having recoverable stretch.

Definitions

As used herein, the term "recoverable stretch" refers to the difference between the stretched dimension of a material following the application of a biasing force and that same dimension upon termination of the biasing force. Percent recoverable stretch may be expressed as [(maximum stretch length−recovered sample length)/recovered sample length]× 100. For example, if a material having a stretched or extended length of 1.85 inches contracts, that is, recovers 0.85 inch to a length of 1 inch, that material can be said to have a recoverable stretch of 85 percent.

As used herein, the term "non-recoverable stretch" refers to elongation of a material upon application of a biasing force which is not followed by a contraction of the material as described above for "recoverable stretch". Non-recoverable stretch may be expressed as follows:

Non-recoverable stretch=100−recovery when the recovery (defined below) is expressed in percent.

As used herein, the term "recovery" refers to the contraction of a stretched material upon termination of a biasing force following stretching of the material by application of the biasing force. For example, if a material having a relaxed, unbiased length of one (1) inch is elongated 50 percent by stretching to a length of one-and-one-half (1.5) inches, the material is elongated 50 percent (0.5 inch) and has a stretched length that is 150 percent of its relaxed length. If this stretched material contracts, that is, recovers to a length of one-and-one-tenth (1.1) inches after release of the biasing and stretching force, the material has recovered 80 percent (0.4 inch) of its one-half (0.5 inch) elongation. Percent recovery may be expressed as [(maximum stretch length final sample length)/(maximum stretch length−initial sample length)]×100.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing and melt spinning processes, spunbonding processes and bonded carded web processes.

As used herein, the term "spunbonded web" refers to web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of Super-Fine organic Fibers" by V. A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, the term "microfibers" means small diameter fibers having an average diameter not greater than about 100 microns, for example, having a diameter of from about 0.5 microns to about 50 microns, more specifically microfibers may also have an average diameter of from about 4 microns to about 40 microns.

As used herein, the term "disposable" is not limited to single use or limited use articles but also refers to articles that are so inexpensive to the consumer that they can be discarded if they become soiled or otherwise unusable after only one or a few uses.

As used herein, the term "garment" refers to protective garments and/or shields including for example, but not limited to, surgical gowns, patient drapes, face masks, shoe covers, diaper outer covers, training pants, coveralls, work suits, aprons and the like.

As used herein, the term "liquid resistant" refers to material having a hydrostatic head of at least about 25 centimeters as determined in accordance with the standard hydrostatic pressure test AATCCTM No. 127-1977 with the following exceptions: (1) The samples are larger than usual and are mounted in a stretching frame that clamps onto the cross-machine direction ends of the sample, such that the samples may be tested under a variety of stretch conditions (e.g., 10%, 20%, 30%, 40% stretch); and (2) The samples are supported underneath by a wire mesh to prevent the sample from sagging under the weight of the column of water.

As used herein, the term "stretchably conformable" refers to material having both measurable softness and recoverable stretch. A stretchably conformable material has softness characterized by a drape stiffness in at least one direction of less than about 2.75 cm. For example, a conformable material may have a drape stiffness in at least one direction from less than about 1.5 up to about 2.75 cm. Drape stiffness is determined using a stiffness tester available from Testing Machines, Amityville, Long Island, N.Y. 11701. Test results are obtained in accordance with ASTM standard test D1388-64 using the method described under Option A (Cantilever Test). A conformable material may have measurable softness which is characterized by cup crush test results of less than about 200 grams. For example, a conformable material may have cup crush test results from less than about 150 up to about 200 grams. The cup crush test evaluates fabric stiffness by measuring the peak load required for a 4.5 cm diameter hemispherically shaped foot to crush a 9"×9" piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. The foot and the cup are aligned to avoid contact between the cup walls and the foot which might affect the peak load. The peak load is measured while the foot descends at a rate of about 0.25 inches per second (15 inches per minute) utilizing a Model FTD-G-500 load cell (500 gram range) available from the Schaevitz Company, Tennsauken, N.J.

As used herein, the term "breathable" refers to material having a Frazier porosity of at least about 25 cubic feet per minute per square foot (cfm/ft²). For example, the Frazier porosity of a breathable material may be from about 25 to more than 45 cfm/ft². The Frazier porosity is determined utilizing a Frazier Air Permeability Tester available from the Frazier Precision Instrument Company. The Frazier porosity is measured in accordance with Federal Test Method 5450, Standard No. 191A, except that the sample size is 8"×8" instead of 7"×7".

As used herein, the term "necked material" refers to any material which has been constricted in at least one dimension by processes such as, for example, drawing.

As used herein, the term "neckable material" means any material which can be necked.

As used herein, the term "reversibly-necked material" refers to a necked material that has been treated while necked to impart memory to the material so that when force is applied to extend the material to its pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination of mixtures thereof. The production of reversibly-necked materials is illustrated in patents such as, for example, Mormon, U.S. Pat. Nos. 4,965,122 and 4,981,747.

As used herein, the term "stretch direction" refers to the direction in which a reversibly-necked material has recoverable stretch (i.e., the direction of stretch and recovery).

As used herein, the term "percent neck down" refers to the ratio determined by measuring the difference between the pre-necked dimension and the necked dimension of a neckable material and then dividing that difference by the pre-necked dimension of the neckable material.

As used herein, the term "percent stretch" refers to the ratio determined by measuring the change in the necked dimension of a reversibly-necked material upon application of a stretching force and dividing that value by the necked dimension before application of the stretching force. For example, the percent stretched may be represented by the following expression:

$$\% \text{ stretch} = [(\text{maximum stretched dimension} - \text{initial necked dimension})/\text{initial necked dimension}] \times 100$$

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates or materials added to enhance processability of a composition.

SUMMARY OF THE INVENTION

The present invention addresses the above-described need by providing disposable protective garments adapted to stretchably conform to the body of a wearer, the garment being composed of a material which is inexpensive, breathable, liquid resistant and has recoverable stretch.

Generally described, the stretchably conformable garment of the present invention is composed of at least one piece of a reversibly-necked material which is adapted to stretch in at least one direction. The reversibly-necked material is necked by drawing and treated to impart memory of its necked configuration. In one aspect of the present invention, the stretchably conformable garment is made of a reversibly-necked material which is adapted to stretch at least about 10 percent in at least one direction, and recover to at least about 80 percent of its original necked dimension. For example, the reversibly-necked material may be adapted to stretch about 15 percent and recover to at least about 95 percent of its original necked dimension. As a further example, the reversibly-necked material may be adapted to stretch about 30 percent and recover about 85 percent of its original necked dimension. Generally speaking, the stretchably conformable garment of the present invention has a recoverable stretch of at least about 10 percent. For example, the stretchably conformable garment may have a recoverable stretch of from about 10 percent to about 30 percent or more.

The stretchably conformable garment of the present invention also has a hydrostatic head of at least about 25 cm, even when the reversibly-necked material is stretched more than 15 percent. For example, the stretchably conformable garment may have a hydrostatic head of at least about 30 cm when the reversibly-necked material is stretched about 20 percent. As a further example, the stretchably conformable garment of the present invention may have a hydrostatic head from about 35 cm to about 45 cm when the reversibly-necked material is stretched about 20 percent. The stretchably conformable garment of the present invention is breathable as characterized by a Frazier porosity of at least about 25 cfm/ft².

The stretchably conformable garment of the present invention also has measurable softness as characterized by a drape stiffness of less than about 2.75 cm and cup crush test results of less than about 200 grams. For example, the stretchably conformable garment of the present invention may have a drape stiffness from less than about 1.5 up to about 2.75 cm and cup crush test results from less than about 150 up to about 200 grams.

In another aspect of the present invention, the stretchably conformable garment is composed of generally planar sections joined by seams, in which at least one of the generally planar sections is a reversibly-necked material that is necked by drawing and treated to impart memory of its necked configuration. The seams may be, for example, conventional stitched seams or seams provided by ultrasonic welding, solvent welding, thermal welding or the like.

In an embodiment of the invention, the stretchably conformable garment may have a body portion, sleeve portions and leg portions extending therefrom. For example, the conformable garment may be a protective suit which includes: (1) a top section having a body portion and sleeve portions extending therefrom, and (2) a bottom section having leg portions. Desirably, the stretch direction of the reversibly-necked material will be generally parallel to the direction of motion of one or more of the body portion, sleeve portions or leg portions. In another aspect of the present invention, the conformable garment may be a gown having a body portion and sleeve portions extending therefrom. Desirably, the stretch direction of the reversibly-necked material will be generally parallel to the direction of motion of one or more of the body portion and sleeve portions.

According to the present invention, the reversibly-necked nonwoven material may be a reversibly-necked bonded carded web, a reversibly-necked web of spunbonded fibers, a reversibly-necked web of meltblown fibers, and a reversibly-necked laminate of at least one web of spunbonded fibers and at least one web of meltblown fibers.

The fibers of the reversibly-necked material may be formed from polyolefins, polyesters, and polyamides. If the fibers are formed from a polyolefin, the polyolefin may be one or more of polyethylene, polypropylene, polybutene, ethylene copolymers, polypropylene copolymers and butene copolymers.

DETAILED DESCRIPTION OF A PREFERRED EMBODIMENT

Figure 1:
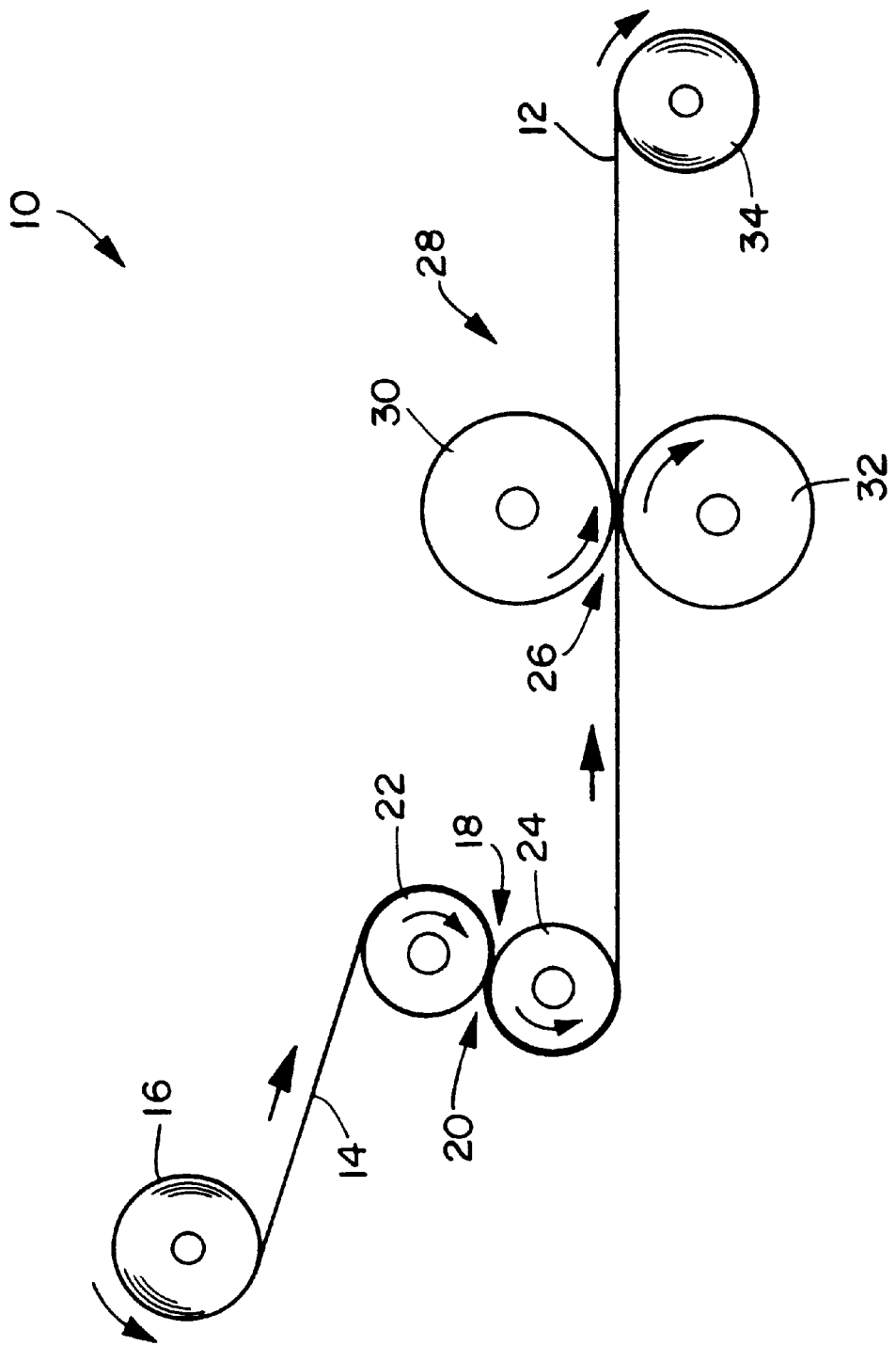
FIG. 1 is a schematic diagram of a portion of an exemplary process for making a reversibly-necked material.

Referring to the drawings in which like reference numerals refer to like elements, there is shown in FIG. 1 an S-roll apparatus 10 which can be used in the process of making a suitable reversibly-necked material 12 for the stretchably conformable garment of the present invention. Exemplary reversibly-necked materials and methods of making such materials are disclosed in, for example, U.S. Pat. No. 4,965,122, incorporated herein by reference. Accordingly, the following discussion will address aspects of reversibly-necked materials and their related processes which generally correlate to the present invention.

A neckable starting material 14 is unwound from a supply roll 16. The neckable starting material 14 then travels in the direction indicated by the arrow associated therewith as the supply roll 16 rotates in the direction of the arrows associated therewith. The neckable material 14 then passes through a nip 18 of an S-roll arrangement 20 formed by stack rollers 22 and 24. Alternatively, the neckable material 14 may be formed by known extrusion processes, such as, for example, known spunbonding or known meltblowing processes, and passed directly through the nip 18 without first being stored on a supply roll.

The neckable material 14 passes through the nip 18 of the S-roll arrangement 20 in a reverse S-wrap path as indicated by the rotation direction arrows associated with the stack rollers 22 and 24. From the S-roll arrangement 20, the neckable material 14 passes through a nip 26 of a drive roller arrangement 28 formed by a pair of drive rollers 30 and 32. Because the peripheral liner speed of the stack rollers 22 and 24 of the S-roll arrangement 20 is controlled to be lower than the peripheral linear speed of the drive rollers 30 and 32 of the drive roller arrangement 28, the neckable material 14 is tensioned between the S-roll arrangement 20 and the nip 26 of the drive roller arrangement 28. By adjusting the difference in the speed of the rollers, the neckable material 14 is tensioned so that it necks a desired amount and may be maintained in such necked condition as it is wound on a wind-up roll 34.

Alternatively, a driven wind-up roll (not shown) may be used so the neckable material 14 may be stretched or drawn between the S-roll arrangement 20 and the driven wind-up roll by controlling the peripheral linear speed of the rollers 22 and 24 of the S-roll arrangement 20 to be lower than the peripheral linear speed of the driven wind-up roll. In yet another embodiment, an unwind having a brake (not shown) which can be set to provide a resistance may be used instead of an S-roll arrangement.

Other methods of tensioning the neckable material 14 may be used such as, for example, tenter frames or various cross-machine direction stretcher arrangements that expand or stretch the neckable material 14 to form the stretchable, resilient, fluid resistant material 12, described below. It will further be understood that the material may be tensioned in such a manner to impart stretchable qualities in more than one direction.

Figure 2:
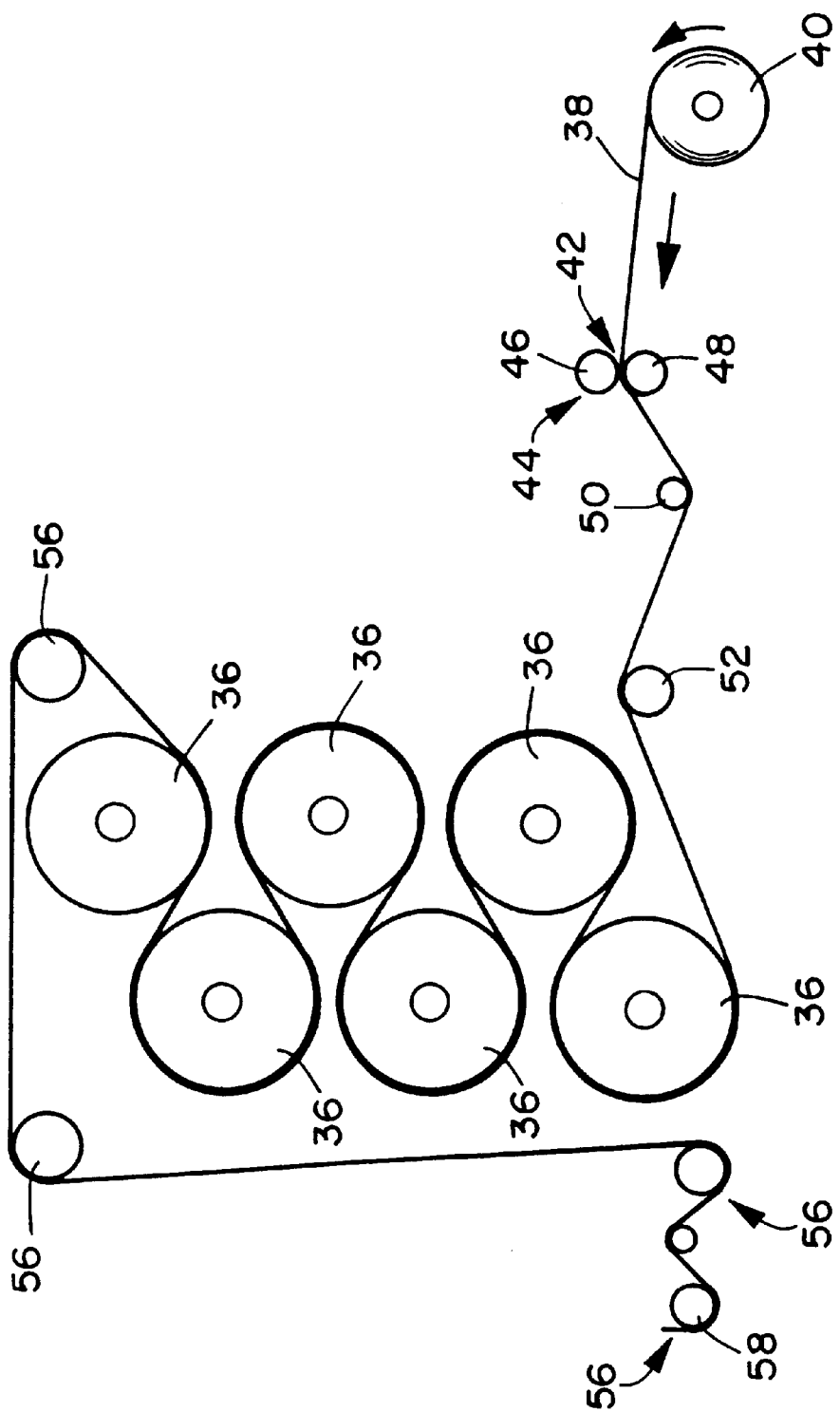
FIG. 2 is a schematic diagram of an exemplary process for making a reversibly-necked material.

While it is understood that a memory of the material's necked configuration may be imparted without the use of heat, it is desirable that heat is used for such purpose. Referring to FIG. 2, there is shown a series of steam cans 36. A neckable material 38 is unwound from a supply roll 40. The neckable material 38 passes through a nip 42 of a drive roller arrangement 44 formed by a pair of drive rollers 46 and 48 and then past two idler rollers 50 and 52.

After passing through the nip 42 of the driver roller arrangement 44 and idler rollers 50 and 52, the neckable material 38 passes over the series of steam cans 36 in a series of reverse S loops. Because the peripheral linear speed of the drive rollers 46 and 48 is controlled to be lower than the peripheral linear speed of the steam cans 36, the neckable material is tensioned between the steam cans 36 and the drive rollers 46 and 48. By adjusting the difference in the speeds of the rollers, the neckable material is tensioned so that it necks a desired amount and is maintained in such necked condition while passing over the steam cans. The neckable material is then cooled in the necked condition after leaving the last steam can. The peripheral linear speed of the rollers of idler rollers 56 are maintained at the same speed as the steam cans 36 so that the necked material is cooled in the necked condition on the way to a wind-up roll 58. This completes formation of the reversibly-necked material 12 having recoverable stretch. Material which has been reversibly-necked as described above might exhibit reduced strength and decreased resistance to tearing when compared to the starting material; however, the reversibly-necked materials generally have sufficient strength and tearing resistance to be suitable for use in protective garments.

The present invention provides a disposable protective garment which is adapted to stretchably conform to the body of a wearer. The garment is composed of a breathable, liquid resistant conformable material 12 having recoverable stretch which is formed as described above to impart stretch and recovery qualities thereto while retaining the liquid resistant, breathable and conformable qualities of the material. Generally speaking, the garment may be composed substantially or entirely of the reversibly necked material. The stretchably conformable garments of the present invention, having recoverable stretch, are particularly well suited for use as protective garments such as, for example, surgical gowns, coveralls, and diapers. Embodiments of the present invention wherein the reversibly-necked material has unidirectional stretch (i.e., ability to stretch and recover generally in one direction) are particularly well suited for such applications because garments made of such material have dimensional stability for ease of donning and yet provide recoverable stretch that adds to the comfort of a wearer. Moreover, the softness and conformability of the reversibly-necked material provides a protective garment that fits closely, produces little noise during movement with minimum bagging and tenting, especially after being worn for an extended period.

In most applications, materials having recoverable stretch of more than about 10 percent are suitable. For example, materials having from about 13 to 20 percent recoverable stretch can be used for coveralls and gowns. In certain applications it may be desirable to use reversibly-necked materials having a level of stretch much greater than 15 percent, such as, for example, reversibly-necked materials that can stretch 75 percent or more as disclosed in previously referenced U.S. Pat. No. 4,965,122. It is contemplated that stretchably conformable garments of the present invention may contain sections, panels, or portions of reversibly-necked materials which may have different degrees of recoverable stretch. For example, a stretchably conformable garment may include a body portion of a reversibly-necked material having a recoverable stretch of about 15 percent and also include attached sleeve portions of a reversibly-necked material having a recoverable stretch much greater than 15 percent (e.g., about 50 percent or more). It is also contemplated that the sleeve portions or other portions (e.g., leg portions, shoulder portions or back portions of a garment) may include sections of reversibly-necked material with very large amounts of recoverable stretch to provide ever greater conformability in the regions of the garment near elbows, knees, shoulders, crotch and other areas where this would be desirable.

In one aspect of the invention, the recoverable stretch of the reversibly-necked material may be non-uniform. This non-uniformity may be intentional or may be caused by limitations of the process equipment. For example, a portion of a reversibly-necked material may be capable of stretching 5 to 15 percent more and/or recovering 5 to 15 percent less than another portion of the same material.

A useful neckable material 14 for the manufacture of the stretchably conformable garments of the present invention is a nonwoven laminated fabric constructed by bonding together layers of spunbonded continuous filaments webs and webs of meltblown fibers (including meltblown microfibers) and may also include a bonded carded web or other nonwoven fabric. This material is so inexpensive to produce that it may be considered to be a disposable material. An exemplary three-layer fabric having a first outer ply of a spunbonded web, a middle ply of a meltblown web, and a second outer ply of a spunbonded web may be referred to in shorthand notation as "SMS". The fibers and/or filaments in such fabrics may be polyolefins, polyesters, and polyamides. If polyolefins are used for the fibers and/or filaments, desirable polyolefins include polyethylene, polypropylene, polybutene, ethylene copolymers, polypropylene copolymers and butene copolymers, as well as blends and copolymers including the foregoing. Desirably, the polyolefin may be a random block copolymer of propylene and ethylene which contains about 3 percent, by weight, ethylene. The fibers and/or filaments may be formed from blends that contain various pigments, additives, strengthening agents, flow modifiers and the like. Such fabrics are described in U.S. Pat. Nos. 4,041,203, 4,374,888, and 4,753,843, the contents of which are incorporated herein by reference. Those patents are assigned to Kimberly-Clark Corporation, the assignee of the present invention.

The neckable material may have a total basis weight of between about 0.75 and about 6.0 ounces per square yard (OSY). For example, the neckable material may have a total basis weight of from about 1.0 to about 3.0 osy. As a further example, the starting material 14 may have a total basis weight from about 1.2 to about 2.0 osy. This material is desirably of spunbond-meltblown-spunbond (SMS) construction in which each layer has a basis weight from about 0.25 to about 2.0 osy. For example, each layer may have a basis weight of from about 0.3 to about 1.0 osy. As a further example, each layer may have a basis weight of from about 0.4 to about 0.8 osy. To improve resistance to liquid and reduce static buildup, the material may also be treated with compositions such as Zepel® and Zelec® K-C, available from E. I. du Pont De Nemours.

EXAMPLE

A neckable SMS material was produced having a weight of 1.48 osy. The polymer used for the spunbond portion was Exxon 9355, a random copolymer of propylene and ethylene containing about 3 percent, by weight ethylene, and the meltblown portion was Exxon 3495 polypropylene, both available form Exxon Company U.S.A., of Houston, Tex. In addition, the material 14 contained about 3 percent TiO$_2$ (titanium dioxide) added as 50 percent concentrate pellets in the extruder.

The starting material was slit to 41 inches and then reversibly necked generally as described in previously referenced U.S. Pat. No. 4,965,122, using conventional equipment. The heating and stretching was done in a heated section of the equipment where the material was festooned around six rolls with a total path length of about 50 feet. The fabric was heated to about 300° Fahrenheit and stretched to produce fabric having a width of about 23 inches, about 27 inches, about 32 inches and about 37 inches, such fabric being further described in Table 1:

TABLE 1

| WIDTH | PERCENT NECK DOWN | RELAXED WEIGHT (OSY) |
|---|---|---|
| 41 Inch | 0 | 1.48 |
| 37 Inch | 9.8 | 1.71 |
| 32 Inch | 22.0 | 1.65 |
| 27 Inch | 34.0 | 1.90 |
| 23 Inch | 43.9 | 2.46 |

Hydrostatic Head

Hydrostatic head tests were performed to determine the liquid resistance of reversibly-necked materials and neckable materials in both relaxed and unrelaxed states.

The results of the hydrostatic head tests are summarized in Table 2:

TABLE 2

| | Hydrostatic Head* in cm at | | | | |
|---|---|---|---|---|---|
| | 0% Stretch | 10% Stretch | 20% Stretch | 30% Stretch | 40% Stretch |
| Starting SMS | 56 | 48 | 33 | ** | ** |
| Reversibly-Necked SMS | | | | | |
| 9.8% neck down | 61 | 62 | 55 | 42 | 31 |
| 22.0% neck down | 64 | 53 | 54 | 44 | 30 |
| 34.0% neck down | 67 | 62 | 58 | 54 | 46 |
| 43.9% neck down | 76 | 68 | 62 | 43 | 43 |

*Average of 5 samples
**Samples would not stretch - - broke.

Recovery

The reversibly-necked samples were also stretched 30 percent in the cross-machine direction (i.e., to about 17 inches) and released to test the ability of the material to recover. The results of the recovery test appear in Table 3:

TABLE 3

| Reversibly-Necked Material | Initial Size | | | Recovered Size | | | Dimensional Change | | |
|---|---|---|---|---|---|---|---|---|---|
| Percent Neck down | MD[1] | x | CD[2] | MD | x | CD | MD | x | CD |
| 9.8% | 9" | | 13" | 9" | | 13 3/8" | 0% | | 2.9% |
| 22.0% | 9" | | 13" | 9" | | 13 3/8" | 0% | | 2.9% |
| 34.0% | 9" | | 13" | 9" | | 13 3/8" | 0% | | 2.9% |
| 43.9% | 9" | | 13" | 9" | | 13 1/4" | 0% | | 1.9% |

[1]designates measurement taken in machine direction.
[2]designates measurement taken in cross-machine direction.

The above description provides materials suitable for use in the construction of stretchably conformable protective garments, especially those requiring breathability. For example, surgical gowns and face masks may be constructed which are comfortable yet resistant to blood and other liquids. Likewise, coveralls, headgear, drapes and the like may be constructed which allow more freedom of movement, conform more closely to the body, and offer resistance to passage of blood and other liquids through the article.

Figure 3:
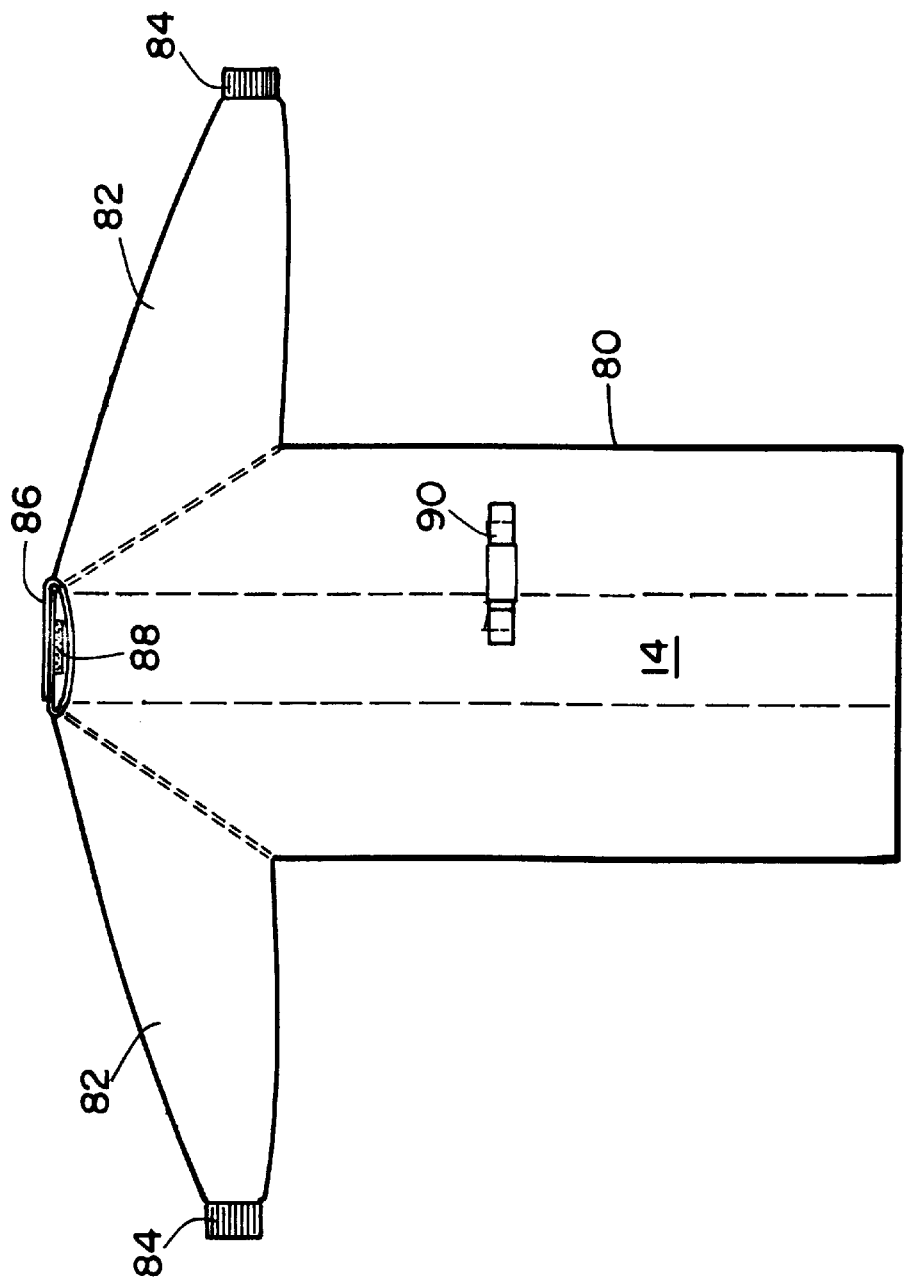
FIG. 3 illustrates an exemplary disposable protective garment in accordance with the present invention.

FIG. 3 illustrates an exemplary disposable surgical gown 80 of the present invention which is adapted to stretchably conform to the body of a wearer and which is made from a reversibly-necked material. The manufacture of such a gown may be-in accordance with known automated, semi-automated, or hand assembly procedures. An example is set forth in U.S. Pat. No. 3,570,012 to Winters, incorporated herein and assigned to the assignee of the present invention. As shown, the gown 80 includes sleeves 82, cuffs 84, neck opening 86 including closure means 88, overlapping back panels, and a belt 90 for closing the gown. The sleeves 82 may be oriented so that the stretched direction of the reversibly-necked material may be either parallel or transverse to the direction of motion (i.e., the length) of the sleeve 82. Each configuration provides certain advantages. For example, if the stretch direction of the sleeve 82 is oriented to be transverse to the direction of motion (i.e., length), the dimensional stability of the sleeve is especially well suited to closed-glove suit up procedures.

The materials described above are also well suited for use in the construction of disposable personal care products such as, for example, disposable diapers and disposable incontinence products which are adapted to stretchably conform to the body of a wearer. The materials are especially well suited as an outer layer for disposable diapers which is comfortable and conformable but retains liquids within the confines of the diaper.

Figure 4:
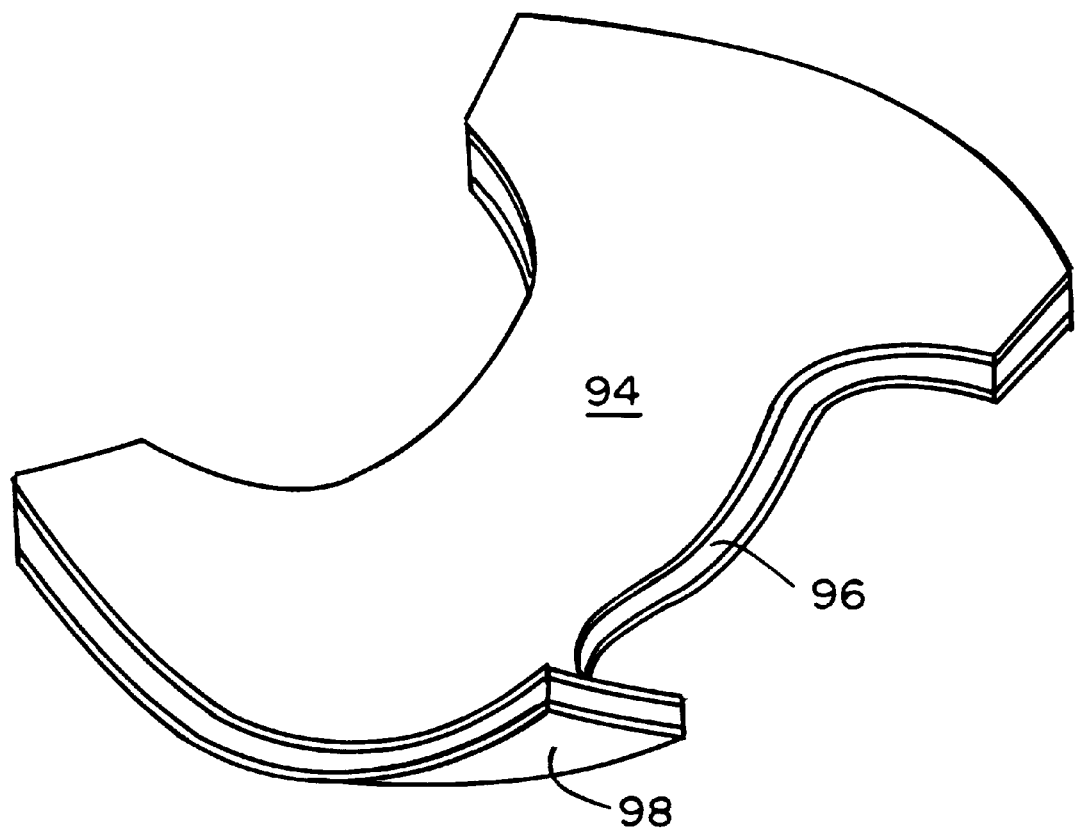
FIG. 4 illustrates an exemplary disposable personal care garment in accordance with the present invention.

FIG. 4 schematically illustrates an exemplary disposable diaper or incontinence product 92 that includes a liner 94, an absorbent medium 96 and a backing material 98. Desirably, the backing material 98 is a reversibly-necked material as described above and is adapted to conform to the body of a wearer. Exemplary disposable diapers and incontinence products are set forth in U.S. Pat. Nos. 3,520,303, 4,701,171, 4,747,846 and 4,756,709 assigned to the assignee of the present invention and incorporated herein by reference.

Figure 5:
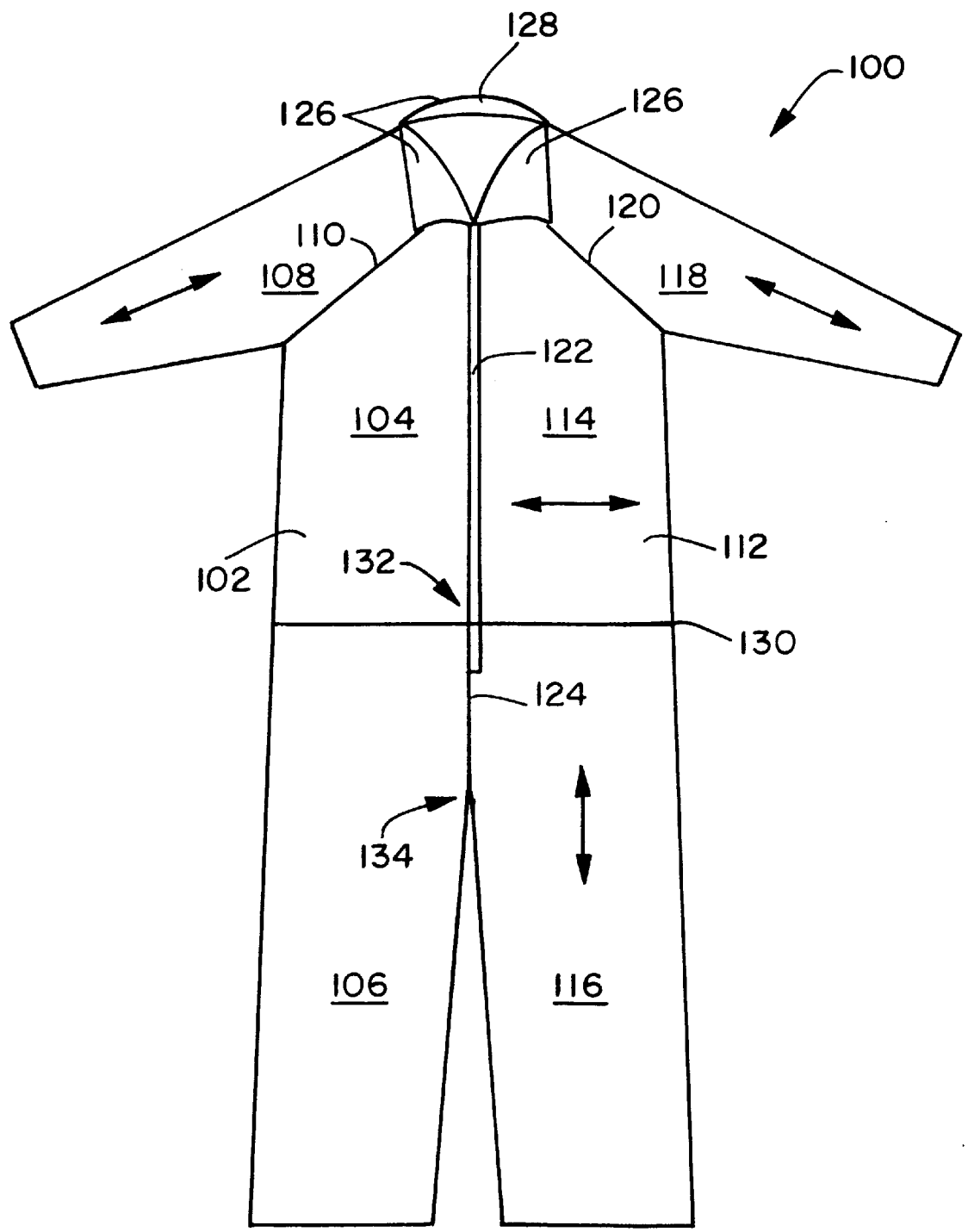
FIG. 5 illustrates exemplary disposable protective coveralls in accordance with the present invention.

FIG. 5 schematically illustrates exemplary disposable protective coveralls 100 of the present invention which are adapted to stretchably conform to the body of a wearer. The coveralls 100 contain a left panel 102 which includes a left body portion 104 and a left leg portion 106. The coveralls contain a left sleeve portion 108 which is joined to the left panel 102 by a seam 110. The coveralls also contain a right panel 112 which includes a right body portion 114 and a right leg portion 116. The coveralls contain a right sleeve portion 118 which is joined to the right panel 112 by a seam 120. The left panel 102 and the right panel are joined by a zipper closure 122 and a seam 124. A collar 126 is attached by a seam 128. Desirably, left panel 102 and right panel 112 are constructed so that seam 130 joins an upper half 132 and a lower half 134. The direction of stretch of the reversibly-necked material in the upper half 132 corresponds to the direction indicated by the arrows associated therewith. The direction of stretch of the reversibly-necked material in the lower half 134 corresponds to the direction indicated by the arrows associated therewith. Similarly, a desired stretch direction of sleeve portions 108 and 118 corresponds to the direction indicated by the arrows associated therewith. Differing constructions are contemplated and various seams and panels of other possible constructions are not shown. An exemplary coverall is set forth in U.S. Pat. No. 4,670,913, assigned to the assignee of the present invention and incorporated herein by reference.

The foregoing description relates to preferred embodiments of the present disposable protective garments which are adapted to stretchably conform to the body of a wearer, and modifications or alterations may be made without departing from the spirit and scope of the invention as defined in the following claims.

What is claimed is:

1. A disposable diaper that stretchably conforms to a wearer, said disposable diaper comprising:

a backing material comprising at least one piece of a reversibly-necked material adapted to stretch in at least one direction to conform to the body of a wearer such that the material is sufficiently liquid resistant to have a hydrostatic head of at least about 25 cm when the material is stretched at least about 15 percent, and wherein stretch direction of the reversibly-necked material is parallel to the direction of motion of a wearer of the disposable diaper, the backing material forming the outer cover of the diaper and defining a waist opening, leg openings, a central crotch section, front and rear panels separated by the crotch section, and a pair of side panels extending between the leg and waist openings and interconnecting the front and rear panels, respectively;

a liquid permeable bodyside liner;

an absorbent medium superposed between the bodyside liner and the backing material; and attachment means for attaching and integrating the bodyside liner and absorbent medium with the backing material.

2. A disposable diaper that stretchably conforms to a wearer, said disposable diaper comprising:

a backing material comprising at least one piece of a reversibly-necked material adapted to stretch in at least one direction to conform to the body of a wearer, the reversibly-necked material being necked by drawing and treated to impart memory of its necked configuration such that the material is sufficiently liquid resistant to have a hydrostatic head of at least about 25 cm when the material is stretched at least about 15 percent, the backing material forming the outer cover of the diaper and defining a waist opening, leg openings, a central crotch section, front and rear panels separated by the crotch section, and a pair of side panels extending between the leg and waist openings and interconnecting the front and rear panels, respectively;

a liquid permeable bodyside liner;

an absorbent medium superposed between the bodyside liner and the backing material; and attachment means for attaching and integrating the bodyside liner and absorbent medium with the backing material.

3. The disposable diaper of claim 2, wherein the reversibly-necked material is selected from the group consisting of a reversibly-necked bonded carded web, a reversibly-necked web of spunbonded fibers, a reversibly-necked web of meltblown fibers, a reversibly-necked laminate of at least one web of spunbonded fibers and at least one web of meltblown fibers and mixtures thereof.

4. The disposable diaper of claim 3, wherein the fibers of the reversibly-necked material comprise a polymer selected from the group consisting of polyolefins, polyesters, and polyamides.

5. The disposable diaper of claim 4, wherein the polyolefin is selected from the group consisting of one or more of polyethylene, polypropylene, polybutene, ethylene copolymers, polypropylene copolymers and butene copolymers.

6. The disposable diaper of claim 2, wherein the reversibly-necked material has a basis weight from about 0.75 to about 6 ounces per square yard.

7. The disposable diaper of claim 1, wherein the reversibly-necked material has a basis weight from about 1.0 to about 3.0 ounces per square yard.

8. The disposable diaper of claim 2, wherein the reversibly-necked material has a hydrostatic head of at least about 30 cm when the material is stretched at least about 20 percent.

9. The disposable diaper of claim 2, wherein the reversibly-necked material has a hydrostatic head of at least about 35 to about 45 cm when the material is stretched at least about 20 percent.

10. The disposable diaper of claim 2 in which the stretch direction of the reversibly-necked material is parallel to the direction of motion of a wearer of the disposable diaper.

11. The disposable diaper of claim 2, wherein the reversibly-necked material is breathable.

12. The disposable diaper of claim 11, wherein the reversibly-necked material has a Frazier porosity of at least about 30 cubic feet per minute per square foot.

13. A disposable personal care product that stretchably conforms to a wearer, said disposable personable care product comprising:

a backing material formed of at least one piece of a reversibly-necked material adapted to stretch in at least one direction, the reversibly-necked material being necked by drawing and treated to impart memory of its necked configuration such that the material is sufficiently liquid resistant to have a hydrostatic head of at least about 25 cm when the material is stretched at least about 15 percent, the backing material forming the outer cover of the personal care product;

a liquid permeable bodyside liner;

an absorbent medium superposed between the bodyside liner and the backing material; and attachment means for attaching and integrating the bodyside liner and absorbent medium with the backing material.

14. The disposable personal care product of claim 13 in the form of a diaper.

15. The disposable diaper of claim 9, wherein the stretch direction of the reversibly-necked material is parallel to the direction of motion of a wearer of the disposable diaper.

16. The disposable personal care product of claim 13, wherein the reversibly-necked material is selected from the group consisting of a reversibly-necked bonded carded web, a reversibly-necked web of spunbonded fibers, a reversibly-necked web of meltblown fibers, a reversibly-necked laminate of at least one web of spunbonded fibers and at least one web of meltblown fibers and mixtures thereof.

17. The disposable personal care product of claim 16, wherein the fibers of the reversibly-necked material comprise a polymer selected from the group consisting of polyolefins, polyesters, and polyamides.

18. The disposable personal care product of claim 17, wherein the polyolefin is selected from the group consisting of one or more of polyethylene, polypropylene, polybutene, ethylene copolymers, polypropylene copolymers and butene copolymers.

19. The disposable personal care product of claim 13, wherein the reversibly-necked material has a basis weight from about 0.75 to about 6 ounces per square yard.

20. The disposable personal care product of claim 19, wherein the reversibly-necked material has a basis weight from about 1.0 to about 3.0 ounces per square yard.

21. The disposable personal care product of claim 13, wherein the reversibly-necked material is breathable.

22. The disposable personal care product of claim 21, wherein the reversibly-necked material has a Frazier porosity of at least about 30 cubic feet per minute per square foot.

23. The disposable personal care product of claim 13 in the form of an incontinence product.

24. The disposable personal care product of claim 13, wherein the reversibly-necked material has a hydrostatic head of at least about 30 cm when the material is stretched at least about 20 percent.

25. The disposable personal care product of claim 13, wherein the reversibly-necked material has a hydrostatic head of at least about 35 to about 45 cm when the material is stretched at least about 20 percent.

26. The disposable personal care product of claim 13 in the form of a training pant.

* * * * *